United States Patent [19]

Stone et al.

[11] Patent Number: 5,265,427
[45] Date of Patent: Nov. 30, 1993

[54] REFRIGERANT RECOVERY SCHEME

[75] Inventors: John B. Stone, Kingwood; George N. Jones, Houston, both of Tex.

[73] Assignee: Exxon Production Research Company, Houston, Tex.

[21] Appl. No.: 904,787

[22] Filed: Jun. 26, 1992

[51] Int. Cl.$^5$ ................................. F25J 3/00
[52] U.S. Cl. .............................. 62/20; 62/24
[58] Field of Search ...................... 62/20, 24

[56] References Cited

U.S. PATENT DOCUMENTS

| | | | |
|---|---|---|---|
| 2,577,617 | 12/1951 | Hudig | 62/20 |
| 3,262,278 | 7/1966 | Thorsten et al. | 62/20 |
| 4,511,382 | 4/1985 | Valencia et al. | 62/20 |
| 4,707,171 | 11/1987 | Bauer | 62/20 |
| 4,713,940 | 12/1987 | Ranke et al. | 62/20 |
| 4,772,301 | 9/1988 | Bauer | 62/20 |
| 4,881,960 | 11/1989 | Ranke et al. | 62/20 |

FOREIGN PATENT DOCUMENTS

| | | |
|---|---|---|
| 928208 | 6/1973 | Canada . |
| 0143267 | 9/1984 | European Pat. Off. . |
| 0254278 | 7/1987 | European Pat. Off. . |
| 1344198 | 2/1970 | United Kingdom . |

*Primary Examiner*—Ronald C. Capossela
*Attorney, Agent, or Firm*—Susan A. McLean

[57] ABSTRACT

A process for obtaining ethane and propane refrigerant from a lean feed gas is disclosed. Said process involves the addition of a small amount of propane to a stream of said lean feed gas, thus widening the phase envelope and increasing the ease of separation of the methane and nitrogen from heavier components.

3 Claims, 2 Drawing Sheets

5,265,427

REFRIGERANT RECOVERY SCHEME

BACKGROUND OF THE INVENTION

In the production of natural gas, such gas can be condensed into an easily transportable liquid natural gas (LNG) via a propane-precooled multicomponent-refrigerant (MCR) process. In such a process, the natural gas is cooled by multiple levels of, first, propane refrigeration, followed by the MCR refrigeration. The product is liquid natural gas at atmospheric pressure and a temperature of $-260°$ F.

The MCR is composed of nitrogen, methane, ethane and propane. These four components are gathered from various sources. The source of the nitrogen for MCR in these LNG refrigeration plants can be an air separation unit; methane is available from the gas feed. The feed gas to most LNG plants typically contains several percent each of ethane and propane which, as is known in the art, can be easily recovered via condensation and distillation for use as refrigerant components. Some natural gases, however, are very lean, containing such small amounts of ethane or propane that no preferential condensation occurs before the main exchanger used in the LNG refrigerant process. LNG plants processing such lean gases presently must import the ethane (or ethylene) and propane required to meet the MCR refrigerant needs. Since LNG plants are typically located remote from other hydrocarbon processing plants, importing these ethane (or ethylene) and propane refrigerants can be a costly and complicated matter.

SUMMARY OF THE INVENTION

This invention comprises a method of recovering ethane and propane refrigerant components, either separately or mixed, from a small stream of the lean feed gases. In the following example the feed gas is as shown in Table 1. As shown in FIG. 1, this gas is expanded to cool the gas and to lower the pressure to a point where a reasonable separation can be obtained. The gas is modified by adding propane to the feed stream until an ethane-rich liquid phase forms in the feed stream (at conventional processing conditions), to allow a separation to occur. Such mixing can occur before or after expansion with no effect on the method of this invention. This admixing greatly expands the two-phase envelope for the feed gas as demonstrated for the Example in the phase envelope plots (FIGS. 2 and 3) for the neat feed gas and the feed gas mixed with two percent propane.

The mixed gas can then be separated in a variety of ways, as would be obvious to one skilled in the art. One method, as is seen in the Example, is to feed this stream into a cryogenic distillation column where the methane is stripped from the heavier components. The condenser duty is supplied by partially vaporizing a small slip stream of the MCR from the main exchanger. The MCR stream is returned to the main cryogenic exchanger to join the main MCR stream. Alternately, a self-refluxing demethanizer could be used. Reboiler duty can be supplied from any low-level heat source. The methane vapor from the overhead of this column is recompressed to feed pressure via the expander-compressor setup. The liquid from this first column is sent to a second distillation column where the ethane and propane are separated. The condenser duty for this second column can be supplied by boiling propane, which is available in the plant. The propane product from the column can be recycled or distilled further as desired to remove the small amount of heavier compounds.

DESCRIPTION OF THE BEST MODE

Figure 1:
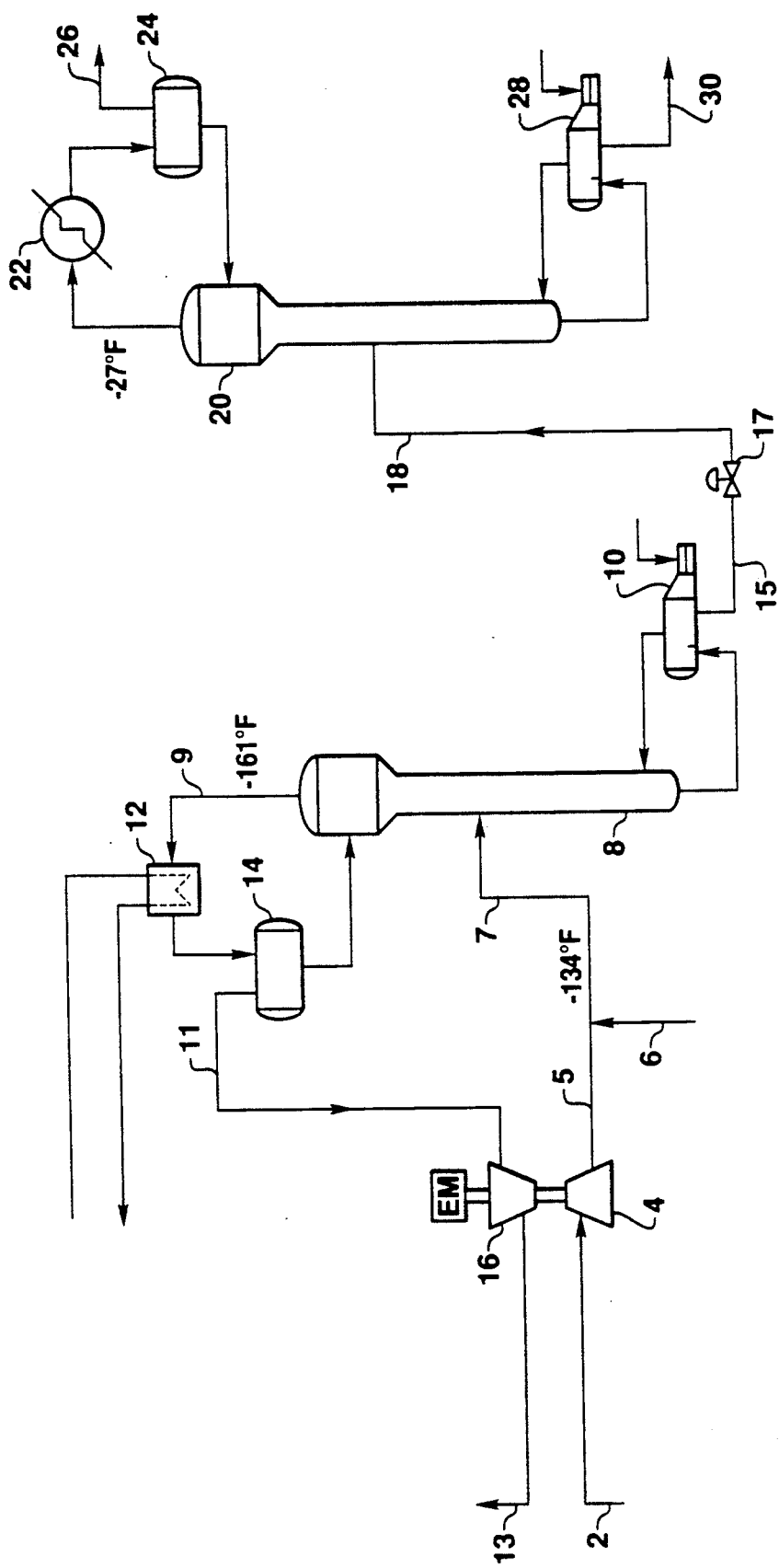
FIG. 1 is a process flow diagram showing a refrigerant separation process of this invention as described in the Example.
Figure 2:
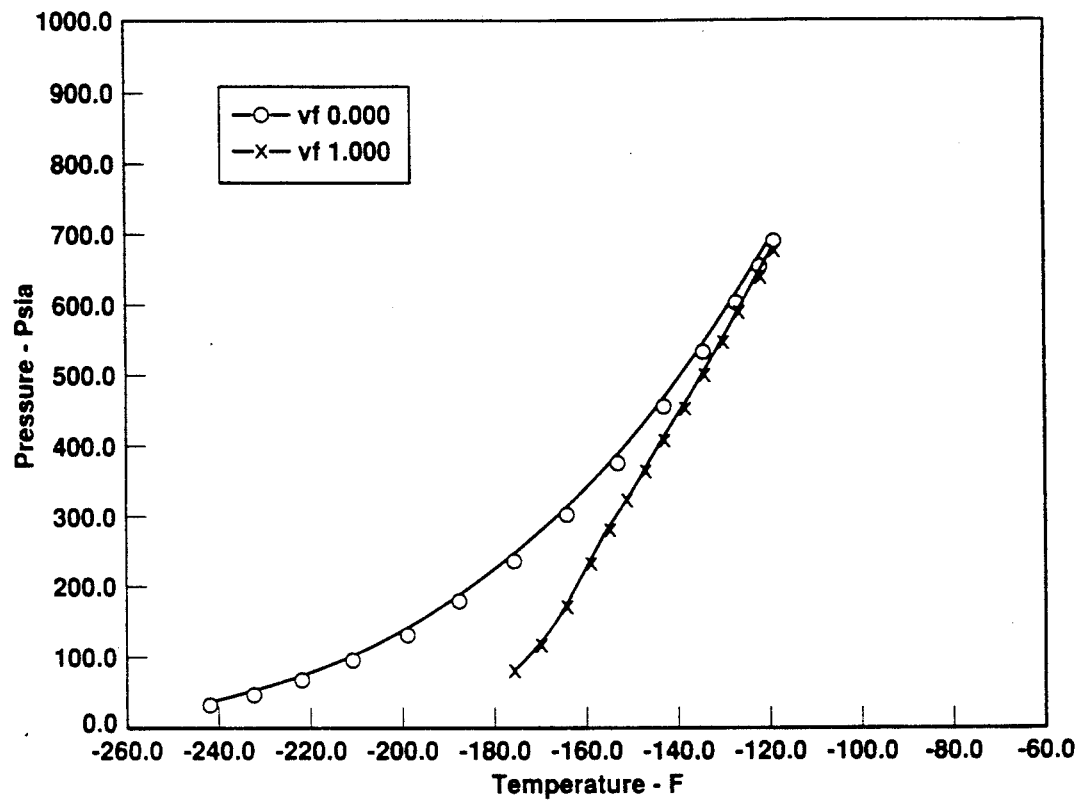
FIG. 2 is a graph of the phase envelope for the lean gas which was the subject gas for the design of this invention.
Figure 3:
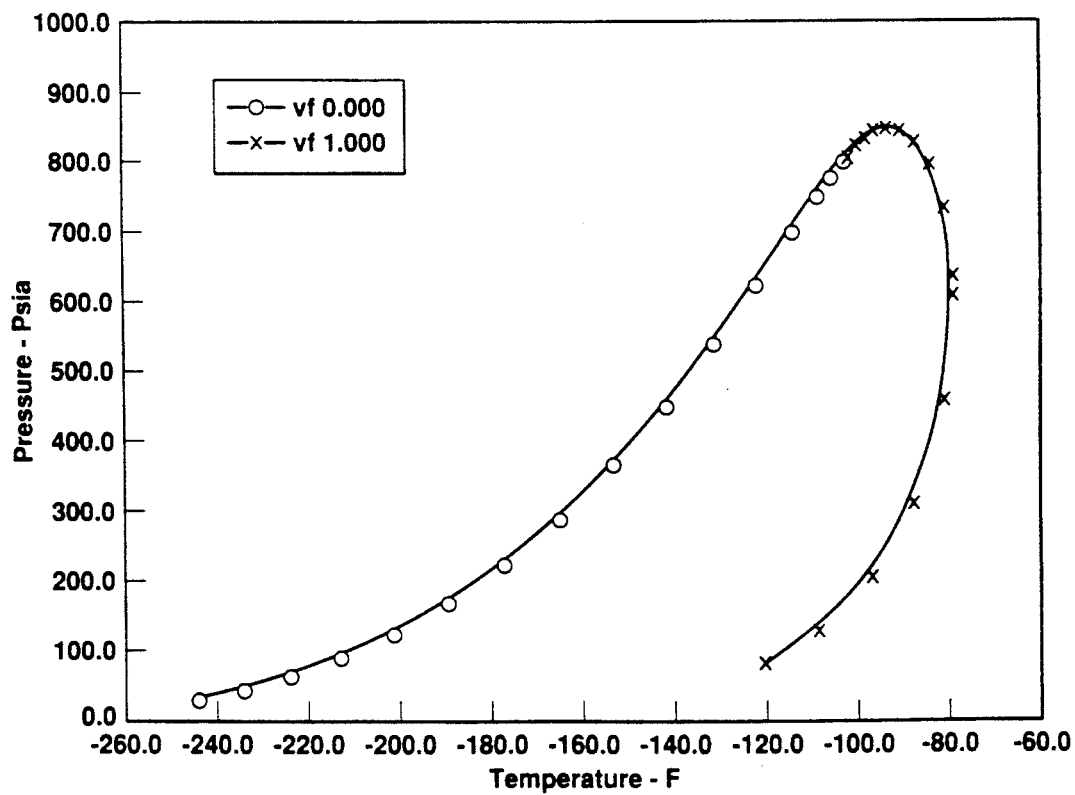
FIG. 3 is a graph of the phase envelope for the same lean gas after addition of propane until the gas was 2% mole propane.

A slip stream 2 is taken from the main feed stream to the refrigeration process of the main part of the plant. This stream would be on the order of about 1% of the total flow to be refrigerated, depending on the amount of ethane needed for the MCR system. The stream 2 is routed through an expander 4, dropping the temperature to about $-134°$ F. To this chilled stream 5 is added propane feed 6. This propane addition can be thought of as a "promoter" and is the heart of this invention. The combined stream 7 is fed to methane stripper 8, which removes methane and nitrogen overhead at $-161°$ F. The overhead stream 9 is condensed via overhead condenser 12, then routed to reflux drum 14 where phase separation takes place. The liquid is refluxed to methane stripper 8, while the gas passes through a compressor, returning it to about 1000 psia and $-20°$ F.

The bottoms of methane stripper 8 are reboiled through reboiler 10, then phase separated. The gas is returned to methane stripper s while the liquid 1B is sent to the ethane stripper 20. Again, separation of ethane from propane is optional.

The overhead is condensed through condenser 22, then phase separated in reflux drum 24. The liquid is refluxed to the ethane stripper 20, while the gas 26, predominantly ethane, is routed to the refrigeration facilities for use as the ethane component of the MCR refrigerant.

The bottoms of ethane stripper 20 are routed through reboiler 28 and phase separated. The gas is returned to the stripper while the liquid 30 is the propane refrigerant which is then sent to the refrigeration facilities.

EXAMPLE

A computer simulation of the design of FIG. 1 was performed using the HYSIM386 process simulator, marketed by Hyprotech, Ltd. The feed stream used was substantially the same as that shown in Table 1.

Table 2 shows the compositions, properties and flow rates of feed stream 2, expanded feed 5, propane addition 6, methane stripper 8 feed 7, methane stripper 8 overhead 11, methane gas product 13, feed 18, methane stripper 8 bottoms 15, ethane stripper 20 feed 18, ethane Stripper 20 overhead 26, and ethane stripper 20 bottoms 30.

A review of these tables indicates that the feed stream is only 0.41% ethane, yet the ethane stripper 20 overhead recovers a 76% ethane stream. In other words, based on a 500 lb mole/hr feed, 2.05 moles/hr of ethane are fed to the system. Recovery is 2.48 lb moles/hr of 76% ethane, or 1.88 lb moles/hr of ethane. The $C_2$ refrigerant stream 26 produced is 2.48 lb moles/hr, and the $C_3$ refrigerant stream produced is 10.10 lb moles/hr, both of which are sufficient to supply the refrigeration needs of multicomponent-refrigerant process.

TABLE 1

FEED GAS COMPOSITION

| Component | Mole % |
|---|---|
| Methane | 98.008 |
| Ethane | 0.4057 |
| Propane | 0.0286 |
| i-Butane | 0.0035 |
| n-Butane | 0.0028 |
| Nitrogen | 1.5517 |

TABLE 2

| Description | | Stream 2 | Stream 5 | Stream 6 |
|---|---|---|---|---|
| Vapor frac. | | 1.0000 | 1.0000 | 0.0000 |
| Temperature | F. | −30.0000* | −143.3254 | −30.0000* |
| Pressure | Psia | 1000.0000* | 300.0000* | 300.0000* |
| Molar Flow | Lbmole/hr | 500.0000* | 500.0000 | 10.0000* |
| Methane | mole frac. | 0.9801* | 0.9801 | 0.0000* |
| Ethane | mole frac. | 0.0041* | 0.0041 | 0.0000* |
| Propane | mole frac. | 0.0003* | 0.0003 | 1.0000* |
| i-Butane | mole frac. | 0.0000* | 0.0000 | 0.0000* |
| n-Butane | mole frac. | 0.0000* | 0.0000 | 0.0000* |
| Nitrogen | mole frac. | 0.0155* | 0.0155 | 0.0000* |

| Description | | Stream 7 | Stream 11 | Stream 15 |
|---|---|---|---|---|
| Vapor frac. | | 0.9556 | 1.0000 | 0.0000 |
| Temperature | F. | −134.2248 | −161.5498 | 82.8275 |
| Pressure | Psia | 300.0000 | 295.0000 | 300.0000 |
| Molar Flow | Lbmole/hr | 510.0000 | 497.4210 | 12.5790 |
| Methane | mole frac. | 0.9608 | 0.9842 | 0.0390 |
| Ethane | mole frac. | 0.0040 | 0.0002 | 0.1517 |
| Propane | mole frac. | 0.0199 | 0.0000 | 0.8065 |
| i-Butane | mole frac. | 0.0000 | 0.0000 | 0.0016 |
| n-Butane | mole frac. | 0.0000 | 0.0000 | 0.0012 |
| Nitrogen | mole frac. | 0.0152 | 0.0156 | 0.0000 |

| Description | | Stream 18 | Stream 26 | Stream 30 |
|---|---|---|---|---|
| Vapor frac. | | 0.1887 | 1.0000 | 0.0000 |
| Temperature | F. | 48.2246 | −27.1812 | 82.7086 |
| Pressure | Psia | 150.0000* | 145.0000 | 150.0000 |
| Molar Flow | Lbmole/hr | 12.5790 | 2.4814 | 10.0976 |
| Methane | mole frac. | 0.0390 | 0.1977 | 0.0000 |
| Ethane | mole frac. | 0.1517 | 0.7614 | 0.0019 |
| Propane | mole frac. | 0.8065 | 0.0409 | 0.9946 |
| i-Butane | mole frac. | 0.0016 | 0.0000 | 0.0020 |
| n-Butane | mole frac. | 0.0012 | 0.0000 | 0.0015 |

TABLE 2-continued

| | | | | |
|---|---|---|---|---|
| Nitrogen | mole frac. | 0.0000 | 0.0000 | 0.0000 |

2 = Feed
5 = Expanded Feed
6 = Propane
7 = Methane Stripper 8 Feed
11 = Methane Stripper 8 Overhead
15 = Methane Stripper
18 = Ethane Stripper 20 Feed
26 = Ethane Stripper 20 overhead
30 = Ethane Stripper 20 Bottoms

What is claimed is:

1. A process for promoting the separation of ethane and heavier hydrocarbons from a gas stream, which process comprises:
   a) removing less than about 2% of the gas stream to be separated, to create a removed stream;
   b) adding to said removed stream a substantially propane feed stream to create a combined stream;
   c) distilling said combined stream to remove a substantially propane product stream; and
   d) routing said substantially propane product stream to refrigeration facilities to be used in the distillation of the balance of the gas stream.

2. A process for promoting the separation of ethane and heavier hydrocarbons from a gas stream, which process comprises:
   a) removing less than about 2% of the gas stream to be separated, to create a removed stream;
   b) adding to said removed stream a substantially propane feed stream to create a combined stream;
   c) distilling said combined stream to remove a substantially ethane stream; and
   d) routing said substantially ethane stream to refrigeration facilities to be used in the distillation of the balance of the gas stream.

3. A process for promoting the separation of ethane and heavier hydrocarbons from a gas stream, which process comprises:
   a) removing less than about 2% of the gas stream to be separated, to create a removed stream;
   b) adding to said removed stream a substantially propane feed stream to create a combined stream;
   c) distilling said combined stream to remove a substantially ethane stream and a substantially propane product stream; and
   d) routing said substantially ethane stream and said substantially propane product stream to refrigeration facilities to be used in the distillation of the balance of the gas stream.

* * * * *